(12) United States Patent
Ritoniemi et al.

(10) Patent No.: US 10,955,347 B2
(45) Date of Patent: Mar. 23, 2021

(54) OPTICAL DETECTION OF FLUORESCENT LIQUID FROM A WOOD FIBRE WEB

(71) Applicant: Procemex Oy, Jyväskylä (FI)

(72) Inventors: Jari Ritoniemi, Pirkkala (FI); Markus Ritoniemi, Tampere (FI)

(73) Assignee: Procemex Oy, Jyväskylä (FI)

( * ) Notice: Subject to any disclaimer, the term of this patent is extended or adjusted under 35 U.S.C. 154(b) by 0 days.

(21) Appl. No.: 15/757,737

(22) PCT Filed: Sep. 6, 2016

(86) PCT No.: PCT/FI2016/050617
§ 371 (c)(1),
(2) Date: Mar. 6, 2018

(87) PCT Pub. No.: WO2017/042432
PCT Pub. Date: Mar. 16, 2017

(65) Prior Publication Data
US 2019/0049381 A1 Feb. 14, 2019

(30) Foreign Application Priority Data
Sep. 8, 2015 (FI) .................................... 20155643

(51) Int. Cl.
*G01N 21/64* (2006.01)
*G01N 21/892* (2006.01)
(Continued)

(52) U.S. Cl.
CPC ........... *G01N 21/6456* (2013.01); *B27K 5/02* (2013.01); *D21G 9/0009* (2013.01);
(Continued)

(58) Field of Classification Search
CPC ............... G01N 21/64; G01N 21/6408; G01N 21/6428; G01N 21/643; G01N 21/6454; G01N 21/6456
See application file for complete search history.

(56) References Cited

U.S. PATENT DOCUMENTS 7,413,633 B2    8/2008  Li et al.
9,372,308 B1 *  6/2016  Saxena ............... C12Q 1/6869
(Continued)

FOREIGN PATENT DOCUMENTS

CN        1934151 A       3/2007
CN        202024868 U    11/2011
(Continued)

OTHER PUBLICATIONS

Wang et al.; The Technology and Application of Fluorescent Tracer for Detecting Leak (4 pages).
(Continued)

*Primary Examiner* — David P Porta
*Assistant Examiner* — Mamadou Faye
(74) *Attorney, Agent, or Firm* — Berggren LLP

(57) ABSTRACT

The invention relates to a method, comprising illuminating an area of a wood fibre web by directing ultraviolet light to an area of the web by an ultraviolet light source, capturing an image of at least part of the illuminated area by an imaging device comprising a colour filter, transmitting image data of the captured image to an image data processing device, and analysing if the captured image comprises a fluorescent liquid stain emitting fluorescent light passed through the colour filter. The invention further relates to a machine vision system and a computer program product for detecting fluorescent liquid stains from a wood fibre web.

21 Claims, 6 Drawing Sheets

(51) Int. Cl.
*D21G 9/00* (2006.01)
*G01N 21/86* (2006.01)
*G01N 21/94* (2006.01)
*G01N 21/89* (2006.01)
*G01N 21/91* (2006.01)
*B27K 5/02* (2006.01)
*G01N 33/34* (2006.01)

(52) U.S. Cl.
CPC ....... *D21G 9/0045* (2013.01); *G01N 21/6428* (2013.01); *G01N 21/86* (2013.01); *G01N 21/89* (2013.01); *G01N 21/892* (2013.01); *G01N 21/91* (2013.01); *G01N 21/94* (2013.01); *G01N 33/346* (2013.01); *G01N 2021/6439* (2013.01); *G01N 2021/8663* (2013.01); *G01N 2021/8917* (2013.01)

(56) References Cited

U.S. PATENT DOCUMENTS

| | | |
|---|---|---|
| 2006/0042742 A1 | 3/2006 | Keller |
| 2006/0144266 A1 | 7/2006 | Brown |
| 2009/0184257 A1* | 7/2009 | Shakespeare ............ G01J 3/36 250/459.1 |
| 2009/0185162 A1 | 7/2009 | Shakespeare et al. |
| 2012/0261592 A1 | 10/2012 | Iftime |
| 2015/0153278 A1 | 6/2015 | Erkelenz |

FOREIGN PATENT DOCUMENTS

| | | |
|---|---|---|
| CN | 102734468 A | 10/2012 |
| CN | 102943406 A | 2/2013 |
| CN | 103140752 A | 6/2013 |
| DE | 102011078010 A1 | 12/2012 |
| EP | 2345887 A2 | 7/2011 |
| EP | 2570260 A1 | 3/2013 |
| EP | 2581492 A1 | 4/2013 |
| GB | 2129125 A | 5/1984 |
| JP | 33918389 A | 8/1991 |
| JP | 2002340807 A | 11/2002 |
| JP | 2009047568 A | 3/2009 |
| JP | 2012047482 A | 3/2012 |
| JP | 2014095024 A | 5/2014 |
| WO | 2007024858 A1 | 3/2007 |
| WO | 2013043780 A1 | 3/2013 |
| WO | 2012074462 A1 | 6/2013 |
| WO | 2014068181 A1 | 5/2014 |
| WO | WO 2014068181 A1 * | 5/2014 ............... D21G 5/00 |
| WO | 2015001196 A1 | 1/2015 |

OTHER PUBLICATIONS

Office action of CN201680052003 dated Dec. 19, 2019 by Chinease Patent Office with translation (24 pages).

Zhang Hong, "Management and maintenace of a pulping and papermaking equipment", pp. 80-83, Chemical Industry Press, Dec. 2003.

Search report of EP16843726.7 issued by European Patent Office dated Feb. 19, 2019, 9 pages.

* cited by examiner

OPTICAL DETECTION OF FLUORESCENT LIQUID FROM A WOOD FIBRE WEB

PRIORITY

This application is a U.S national application of the international application number PCT/FI2016/050617 filed on Sep. 6, 2016 and claiming priority of Finnish national application FI20155643 filed on Sep. 8, 2015, the contents of both of which are incorporated herein by reference.

FIELD OF THE INVENTION

The present invention relates to a method for the imaging of continuous wood fibre web, in which method a camera is used for optically detecting fluorescent liquid from the web using UV illumination.

The invention also relates to a system for imaging of continuous wood fibre web, wherein the system comprises a camera and an UV light, and wherein the camera is used for optically detecting fluorescent liquid from the web using UV illumination.

BACKGROUND

In continuous manufacturing processes, for example, paper, pulp and cardboard machines, there are materials or products constantly formed and moving through the machine in a continuous material web. In such processes, the product must be monitored in order to detect possible deviations, for example, oil stains, and to obtain a final product of high quality, for example, by machine vision systems such as camera systems. As the material web moves past the camera system, it is illuminated by a visible light source, and images of it are captured by an imaging device. The captured images are analysed by a processing unit.

SUMMARY

Now there has been invented an improved method and technical equipment implementing the method. Various aspects of the invention include a method, a machine vision system comprising at least one imaging device and an ultraviolet (UV) light source, and a computer readable medium comprising a computer program stored therein, which are characterized by what is stated in the independent claims. Various embodiments of the invention are disclosed in the dependent claims.

According to a first aspect of the invention, there is provided a method, comprising illuminating an area of a wood fibre web by directing ultraviolet light to an area of the web by an ultraviolet light source, capturing an image of at least part of the illuminated area by an imaging device comprising a colour filter, transmitting image data of the captured image to an image data processing device, and analysing if the captured image comprises a fluorescent liquid stain emitting fluorescent light passed through the colour filter.

According to an embodiment, the method further comprises illuminating the area of the wood fibre web by directing non-ultraviolet light to the area of the web by a non-ultraviolet light source after capturing the image illuminated by the ultraviolet light source, capturing an image of at least part of the non-ultraviolet illuminated area by the imaging device, and analysing if the captured non-ultraviolet illuminated image comprises a non-fluorescent defect. According to an embodiment, every other captured image is illuminated with the ultraviolet light and every other with the non-ultraviolet light. According to an embodiment, a part of the captured images are illuminated with the ultraviolet light and the other part with the non-ultraviolet light. According to an embodiment, the wood fibre web is a paper or cardboard web. According to an embodiment, the colour filter is added in front of a lens of an imaging device. According to an embodiment, the filter is a part of the imaging device or an imaging sensor of the imaging device. According to an embodiment, the colour filter is a green filter passing through wavelengths approximately 520-550 nm. According to an embodiment, the colour filter is a red filter passing through wavelengths approximately 640-730 nm. According to an embodiment, the fluorescent liquid stain is leaked from a machine producing the web. According to an embodiment, the fluorescent liquid is produced by adding a fluorescent marker into liquid. According to an embodiment, the fluorescent liquid is inherently fluorescent. According to an embodiment, the fluorescent light emitted by the fluorescent liquid corresponds wavelengths passed through the colour filter. According to an embodiment, the method further comprises increasing the intensity level of the captured image. According to an embodiment, the method further comprises simultaneous detecting of non-fluorescent defects, wherein the non-fluorescent defects are holes, spots, streaks or wrinkles. According to an embodiment, the method further comprises simultaneous detection of the edge of the web. According to an embodiment, the non-ultraviolet light source is a LED.

According to a second aspect of the invention, there is provided a machine vision system for detecting liquid stains from a wood fibre web wherein, said liquid stains arranged to be detected are fluorescent and that the machine vision system comprises an imaging device comprising a colour filter and an ultraviolet light source, wherein the ultraviolet light source is configured to direct ultraviolet light to an area of the web, and wherein the imaging device is configured to capture an image of the area with the filter and to transmit image data of the captured image to an image data processing device for analysing if the captured image comprises a fluorescent liquid stain emitting fluorescent light at wavelength spectrum passing through the colour filter.

According to an embodiment, the system further comprises at least one additional light source directing non-ultraviolet light, wherein the at least one light source is configured to direct non-ultraviolet light to an area of the web, and wherein the imaging device is configured to capture an image of the non-ultraviolet illuminated area after capturing the ultraviolet illuminated image and to transmit image data of the captured image to an image data processing device for analysing for detecting non-fluorescent defects. According to an embodiment, every other captured image is illuminated with ultraviolet light and every other with non-ultraviolet light. According to an embodiment, a part of the captured images are illuminated with ultraviolet light and the other part with non-ultraviolet light. According to an embodiment, the wood fibre web is a paper or cardboard web. According to an embodiment, the colour filter is added in front of a lens of an imaging device. According to an embodiment, the filter is a part of the imaging device or an imaging sensor of the imaging device. According to an embodiment, the colour filter is a green filter passing through wavelengths approximately 520-550 nm. According to an embodiment, the colour filter is a red filter passing through wavelengths approximately 640-730 nm. According to an embodiment, the fluorescent liquid stain is leaked from a machine producing the web. According to an embodiment, the fluorescent liquid is produced by adding a fluorescent marker into liquid. According to an embodiment, the fluorescent liquid is inherently fluorescent. According to an embodiment, the fluorescent light emitted by the fluorescent liquid corresponds wavelengths passed through by the colour filter. According to an embodiment, the imaging device is further configured to increase the intensity level of the captured image. According to an embodiment, the imaging device is further configured to simultaneously detect non-fluorescent defects, wherein the non-fluorescent defects are holes, spots, streaks or wrinkles. According to an embodiment, the imaging device is further configured to simultaneously detect the edge of the web. According to an embodiment, the non-ultraviolet light source is a LED.

According to a third aspect of the invention, there is provided a computer program product embodied on a non-transitory computer readable medium, comprising computer program code configured to, when executed on at least one processor, cause a system to illuminate an area of a wood fibre web by directing ultraviolet light to an area of the web by an ultraviolet light source, capture an image of at least part of the illuminated area by an imaging device comprising a colour filter, transmit image data of the captured image to an image data processing device, and analyse if the captured image comprises a fluorescent liquid stain emitting fluorescent light passed through the colour filter. According to an embodiment, the method further comprises illuminating the area of the wood fibre web by directing non-ultraviolet light to the area of the web by a light source after capturing the image illuminated by the ultraviolet light source, capturing an image of at least part of the non-ultraviolet illuminated area by the imaging device, and analysing if the captured non-ultraviolet illuminated image comprises a non-fluorescent defect. According to an embodiment, every other captured image is illuminated with the ultraviolet light and every other with the non-ultraviolet light. According to an embodiment, a part of the captured images are illuminated with the ultraviolet light and the other part with the non-ultraviolet light. According to an embodiment, the wood fibre web is a paper or cardboard web. According to an embodiment, the colour filter is added in front of a lens of an imaging device. According to an embodiment, the filter is a part of the imaging device or an imaging sensor of the imaging device. According to an embodiment, the colour filter is a green filter passing through wavelengths approximately 520-550 nm. According to an embodiment, the colour filter is a red filter passing through wavelengths approximately 640-730 nm. According to an embodiment, the fluorescent liquid stain is leaked from a machine producing the web. According to an embodiment, the fluorescent liquid is produced by adding a fluorescent marker into liquid. According to an embodiment, the fluorescent liquid is inherently fluorescent. According to an embodiment, the fluorescent light emitted by the fluorescent liquid corresponds wavelengths passed through the colour filter. According to an embodiment, the system is further configured to increase the intensity level of the captured image. According to an embodiment, the system is further configured to simultaneously detect non-fluorescent defects, wherein the non-fluorescent defects are holes, spots, streaks or wrinkles. According to an embodiment, the system is further configured to simultaneously detect the edge of the web.

DESCRIPTION OF THE DRAWINGS

In the following, various embodiments of the invention will be described in more detail with reference to the appended drawings, in which.

DESCRIPTION OF EXAMPLE EMBODIMENTS

Figure 1A:
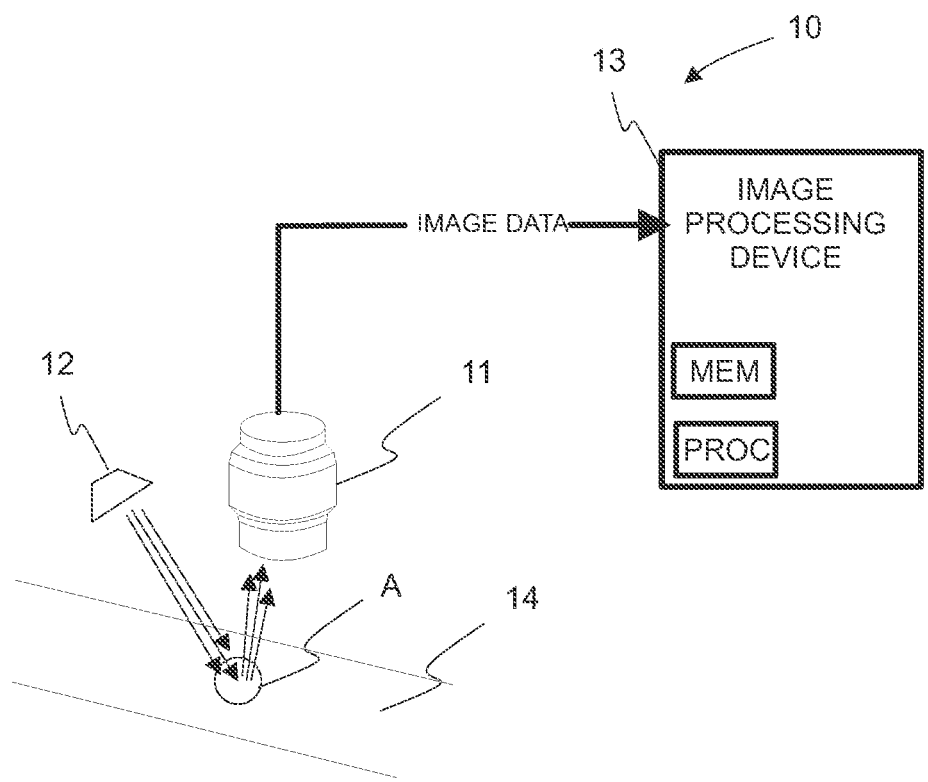
FIG. 1a shows a machine vision system according to the example embodiment.

The present invention relates to a machine vision system according to an example embodiment and comprising at least one imaging device and possibly one or more ultraviolet (UV) light source(s), used for detecting fluorescent liquid from a wood fibre web illuminated with UV light. The term "wood fibre" includes in this context any suitable wood fibre webs, for example, paper, or cardboard webs. The imaging device is used for capturing images of a moving object i.e. a wood fibre web arranged to be monitored. The imaging device of the machine vision system may be, for example, a camera, for example, a c-mos or ccd camera, a matrix or line scan camera, a black and white or colour camera, a regular or smart camera, or any suitable camera. The UV light source emitting UV light may be, for example, UV light emitting diodes (LEDs). The UV light source may preferably emit UV light having a wavelength of 370-400 nm. Lower frequencies can cause accumulation of insects around the UV light source, whereas at higher frequencies the fluorescence effect diminishes. One or more UV light source(s) may also be external from the system.

In factory circumstances, there can be machine liquid spills and leaks, which need to be detected but also distinguished from other objects and defects on the web. From further on the term liquid covers all machine liquids, for example, oils and coolants. The effective way of detecting liquid stains from a wood fibre web and distinguishing liquid stains from other stains on the web is to use fluorescent liquids in machines of the factory. Fluorescent liquid may be produced by adding a fluorescent marker i.e. substance in non-fluorescent liquid or fluorescent liquid may be inherently fluorescent. The idea of the fluorescent marker is to change non-fluorescent liquid to fluorescent liquid. The fluorescent marker may be, for example, UV dye. The liquid stain is caused by oil or other machine liquid spill or leak. The UV light causes a fluorescence response in the liquid stain and the liquid stain can then be more clearly and more reliably detected by at least one imaging device of the machine vision system with respect to non-fluorescent objects and defects.

The at least one imaging device of the machine vision system configured to detect fluorescent liquid stains of a wood fibre web may be equipped with a colour filter that limits non-appropriate wavelengths and passes appropriate wavelengths. The filter is selected to be suitable for the fluorescent light emitted by the used fluorescent liquid so that the fluorescent liquid appears brighter than the web in the captured image(s), or the used fluorescent liquid is selected to be suitable for the used filter. In other words, the filter is arranged to pass the fluorescent emission produced by the fluorescent liquid i.e. by the fluorescent marker of the liquid or the inherently fluorescent liquid, while filtering other wavelengths, for example the UV light reflected from the web. The colour filter may be, for example, a basic green filter passing wavelengths approximately 520-550 nm or a basic red filter passing wavelengths approximately 630-740 nm. The colour filter may be added in front of a lens of an imaging device. The filter may be made of coloured glass or suitable coloured plastic or it may be an adjustable filter or an interference filter suitable for acting as a band pass filter for above mentioned filters. The filter may also be inbuilt to an imaging device meaning that the filter may be a part of the imaging device or an imaging sensor of the imaging device. For example, a colour sensor of the imaging device may be used for filtering non-green colours from image(s) exposed by the sensor, which can act in the same way as an external green filter would. The filter of any mentioned type may also be such that it is specifically chosen for the used fluorescent liquid, in which case passed/limited wavelength(s) may depend on properties of the used fluorescent liquid.

Typically, the fluorescence peak of the fluorescent liquid having a green fluorescence response for UV light is around 500 nm and the fluorescence peak of the fluorescent liquid having a red fluorescence response for UV light is around 700 nm. Therefore, the passband at which the green filter lets light through (>50%) may be, for example, 520-550 nm and the passband at which the red filter lets light through (>50%) may be, for example, 630-740 nm. In other words, passband is a wavelength range i.e. the specific part of the spectrum. Other parts of the spectrum are attenuated. However, it is also possible to use high pass filters in addition to band pass filters. In case of the fluorescent liquid having a green fluorescence response for UV light (~520-550 nm), the filter may pass, for example, signals with a frequency higher than 520 nm and in case of the fluorescent liquid having a red fluorescence response for UV light (~640-730 nm), the filter may pass, for example signals with a frequency higher than 640 nm.

Capturing an image using a colour filter, for example, an additional colour filter or a colour sensor, makes the non-fluorescent parts of the image darker, and the image darker overall. Therefore, the intensity level of the captured images may be increased in order to make them more suitable for inspection. Increasing the intensity level multiplies the brightness values of the image. The intensity level may be increased, for example, by increasing the duration or intensity of light exposure or by adding gain to the image. When the intensity level is increased, the different parts of the image may be seen and differentiated more clearly, for example the fluorescent stain, possible non-fluorescent defects, the web, and the possible edge(s) of the web.

A machine vision system according to embodiments may be arranged, for example, in web monitoring beams or web monitoring rails supporting one or more imaging device and one or more UV lights.

The present invention further relates to a method according to an example embodiment of the invention, wherein one or more image(s) of the web are captured by one or more imaging device(s) while an ultraviolet light illuminates the capturing area, and one or more captured image(s) are analysed by the imaging device and/or transmitted to an external image data processing device for analysis. If a bright area on the web caused by the fluorescent liquid is detected, an alarm may be triggered. The imaging device and/or external image data processing device may also be configured to detect other faults than fluorescent liquid stains simultaneously and alarm about them. Other faults may be, for example, holes, grey or dark spots, streaks or wrinkles. The system may also be used for detecting the edge of the web.

In addition to one or more UV lights, one or more additional non-UV light sources may be used to aid the detection of the non-fluorescent faults i.e. defects. These additional light sources may be, for example, regular non-UV LEDs. The light sources may alternate, for example, so that every other image is illuminated with UV light and every other with regular non-UV light or so that every third, fourth or fifth image is captured while non-ultraviolet light is used or so that every third, fourth or fifth image is captured while ultraviolet light is used. In other words, a part of the captured images are illuminated with ultraviolet light and the other part with non-ultraviolet light.

The imaging device may be a so called smart camera comprising an image data processing device part arranged to analyse captured images. The image data processing device part may comprise at least one processor, at least one memory including computer program code for one or more program units, and means for transferring trigger signals or captured image data wirelessly or via wired connection, for example, a transmitter or a transceiver. There may be multiple processors e.g. a general purpose processor and a graphics processor and a DSP processor and/or multiple different memories e.g. volatile memory for storing data and programs at run-time and non-volatile memory like a hard disk for permanently storing data and programs. The image data processing device part of the imaging device may be any computing device suitable for handling image data such as a computer. The imaging device may also include a video controller and an audio controller for generating signals that can be produced to the user with computer accessories. The smart camera produces output to the user through output means. The video controller may be connected to a display. The display may be e.g. a flat panel display or a projector. The audio controller may be connected to a sound source such as loudspeakers or earphones.

The external image data processing device may be a part of the machine vision system according to embodiments of the invention. The external image data processing device comprises at least one processor, at least one memory including computer program code for one or more program units, and means for receiving image data wirelessly or via wired connection, for example, a receiver or a transceiver and means for transferring trigger signals or image data wirelessly or via wired connection, for example, a transmitter or a transceiver. There may be multiple processors e.g. a general purpose processor and a graphics processor and a DSP processor and/or multiple different memories e.g. volatile memory for storing data and programs at run-time and nonvolatile memory like a hard disk for permanently storing data and programs. The image data processing device may be any computing device suitable for handling image data such as a computer. The connection between the camera and the image data processing device may be a wired or wireless network. The image data processing device may also include a video controller and an audio controller for generating signals that can be produced to the user with computer accessories. The simulator produces output to the user through output means. The video controller may be connected to a display. The display may be e.g. a flat panel display or a projector. The audio controller may be connected to a sound source such as loudspeakers or earphones.

The image data processing device part and/or the external image data processing device may analyse the received image data and if the image data processing device part or the external image data processing device detects a fluorescent liquid stain, the image data processing device part or the external image data processing device may trigger an alarm indicating about the liquid stain.

Figure 1B:
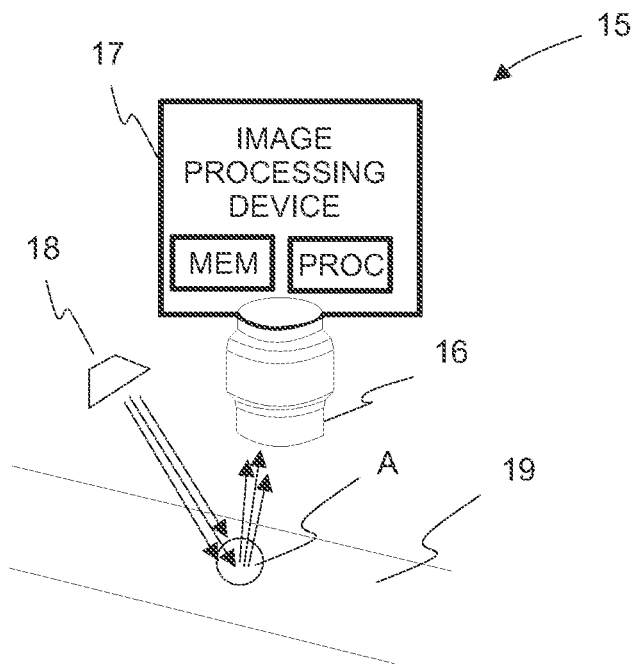
FIG. 1b shows a machine vision system according to the example embodiment.

FIGS. 1a and 1b show a machine vision system according to the example embodiment of the invention. The machine vision system 10 of FIG. 1a comprises an imaging device 11 comprising a filter (not shown), an UV light source 12 and an external image data processing device 13. In this example embodiment there is only one imaging device 11 and one UV light source 12, however it is also possible for there to be two or more imaging devices 11 and/or UV light sources 12. The UV light source 12 illuminates an area of the web 14. In this example embodiment, the area comprises a fluorescent liquid stain A. The imaging device 11 is arranged to capture images from the UV illuminated area of the web 14 through the filter, wherein the filter may be an additional colour filter, for example, green or red filter depending on the used fluorescent liquid, in front of the lens of the imaging device 11 or it may also be a colour sensor of the imaging device 11 filtering, for example, non-green or non-red colours from the image. The intensity level of the images captured with a colour sensor or a colour filter may be increased, for example, by increasing light exposure or by adding gain to the image. After the imaging device 10 has captured at least one image, it transmits the image data to the external image data processing device 13. The image data processing device 13 is configured to analyse the image data that it receives in order to find fluorescent liquid stains. If the external image data processing device 13 detects a fluorescent liquid stain(s), it may trigger an alarm. The external image data processing device 13 may also be configured to detect other faults than fluorescent liquid stains simultaneously and alarm about them.

The machine vision system 15 of FIG. 1b comprises an imaging device 16 comprising an integrated image data processing device 17 and a filter (not shown), and an UV light source 18. In this example embodiment there is only one imaging device 16 and one UV light source 18, however it is also possible for there to be two or more imaging devices 16 and/or UV light sources 18. The UV light source 18 illuminates an area of the web 19 which in this example contains a fluorescent liquid stain A. The imaging device 16 is arranged to capture images from the UV illuminated area of the web 19 through the filter, wherein the filter may be an additional colour filter, for example, green or red filter depending on the fluorescent liquid, in front of the lens of the imaging device 16 or it may also be a colour sensor of the imaging device 16 filtering, for example, non-green or non-red colours from the image. The intensity level of the images captured with a colour sensor or a colour filter may be increased, for example, by increasing light exposure or by adding gain to the image. After the imaging device 16 has captured at least one image, it transmits image data to the integrated processing device 17 that is configured to analyse the image data in order to find fluorescent liquid stains. If the integrated image data processing device 17 detects a fluorescent liquid stain(s), it may trigger an alarm. The integrated image data processing device 17 may also be configured to detect other faults than fluorescent liquid stains simultaneously and alarm about them.

FIGS. 1a and 1b show also the UV light that is emitted by UV light sources 12, 18. It is also shown, how the emitted UV light reflects to the imaging devices 11, 16.

Figure 2A:
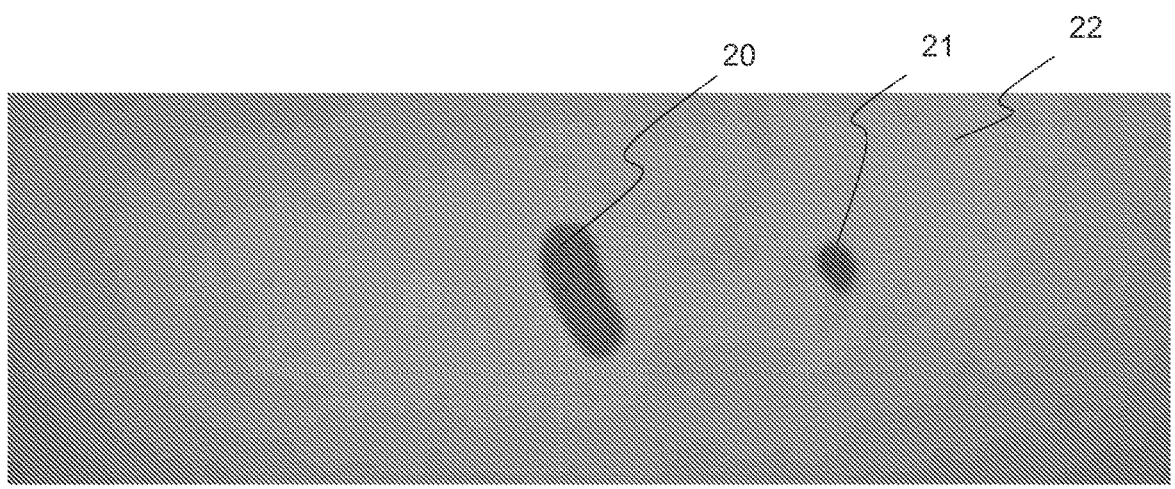
FIG. 2a shows an image of a fluorescent liquid stain of a web captured by a prior art machine vision system.
Figure 2B:
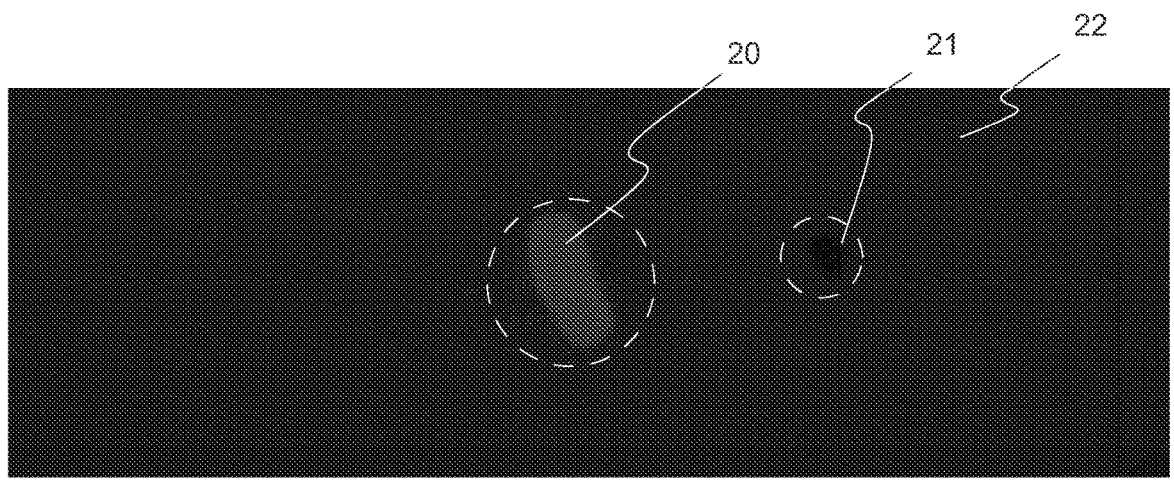
FIG. 2b shows an image of the fluorescent liquid stain of FIG. 2a captured by a machine vision system comprising a colour filter according to the example embodiment of the invention.

FIG. 2a shows an image of a fluorescent liquid stain 20 and a non-fluorescent stain 21 of a wood fibre web 22 captured by an existing machine vision system and 2b shows an image of the same fluorescent liquid stain 20 of the web 23 captured by an imaging device of a machine vision system according to the example embodiment of the invention. FIG. 2a is captured by an imaging device without a colour filter, for example, an additional green or red filter or a colour sensor that filters non-green or non-red colours from the image. Whereas, FIG. 2b is captured by an imaging device comprising either an additional green filter or a colour sensor that filters non-green colours from the image. In addition, a fluorescent liquid used in a machine(s) is selected so that it emits fluorescent light between 520-550 nm that is in green wavelengths' spectrum. As can be seen from FIG. 2b, use of the colour filter or colour sensor makes the non-fluorescent parts of the image darker, and the image darker overall. Therefore it might be more difficult to detect and differentiate parts of the image, like the web 22, the fluorescent liquid stain 20 that is now lighter than the web, and the non-fluorescent stain 21.

Figure 2C:
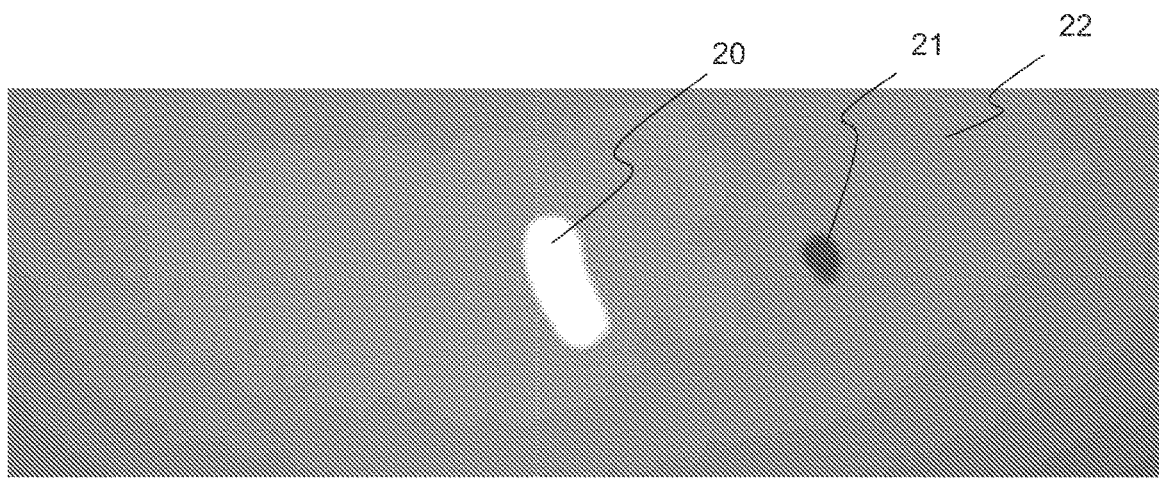
FIG. 2c shows the image of the fluorescent liquid stain of FIG. 2b after increasing the intensity level of the image according to the example embodiment of the invention.

However, the intensity level of the captured image can be increased, for example, so that the web 22 is around the same brightness as in FIG. 2a. FIG. 2c shows the image of FIG. 2b after an increase in intensity level. As can be seen from the image, use of the additional green filter or suitable colour sensor greatly increases the contrast between the fluorescent liquid stain 20 and the non-fluorescent stain 21 or the web 22 and the brightness of the liquid stain 20 compared to the non-fluorescent stain 21 or the web 22.

Figure 3A:
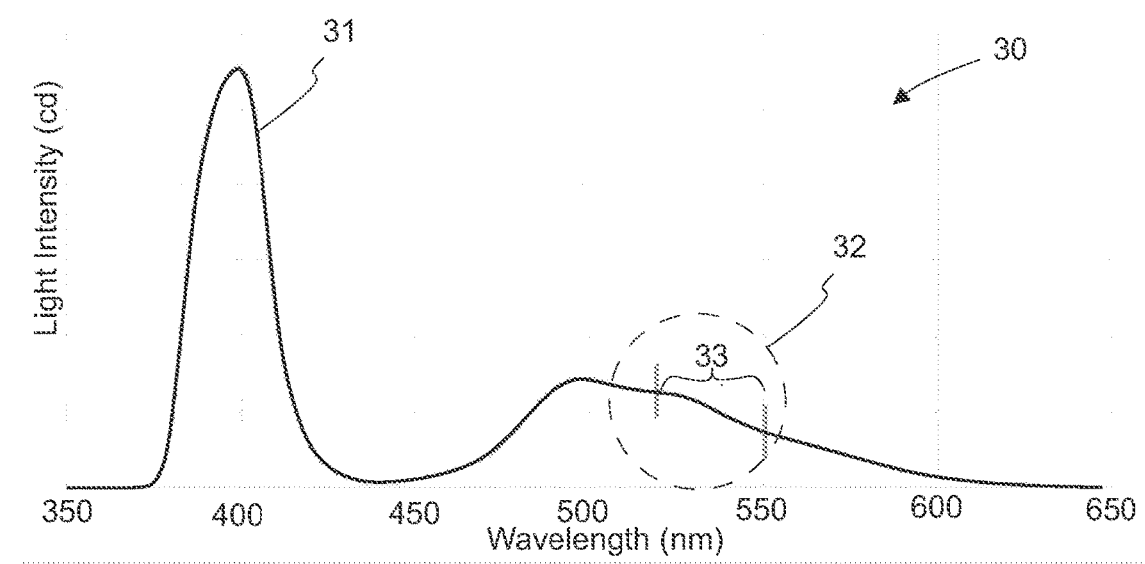
FIG. 3a shows a spectral response of an UV light reflected from a web containing a fluorescent liquid stain.

FIG. 3a shows a spectral response of an UV light 30 reflected from a web containing a fluorescent liquid stain. The light intensity is shown as a function of the wavelength of the light. In this example, a fluorescent liquid is selected so that it emits fluorescent light between 520-550 nm that is in green wavelengths' spectrum. As can be seen from the FIG. 3a, at around 400 nm there is a first intensity peak 31, which is caused by UV light that is reflected from the surface of the imaging target, for example, a web. Whereas, a fluorescence peak 32 emitted by the fluorescent liquid stain existing in the web lies at around 520-550 nm. In order to remove this first peak 31 from the spectral response 30, a filter, which may be an additional green filter in front of the imaging or a colour sensor that filters non-green colours is used. It is preferable to remove this first intensity peak 31 in order to ensure that the fluorescence peak 32 emitted by the fluorescent liquid stain will be seen more brightly than the web. The passband 33 of the filter may be, for example, 520-550 nm. The suitable filter may pass over 50% of light in its passband. Other parts of the spectrum are attenuated. The second peak 32 falls to the passband 33 and will therefore be seen clearly by the imaging device.

Figure 3B:
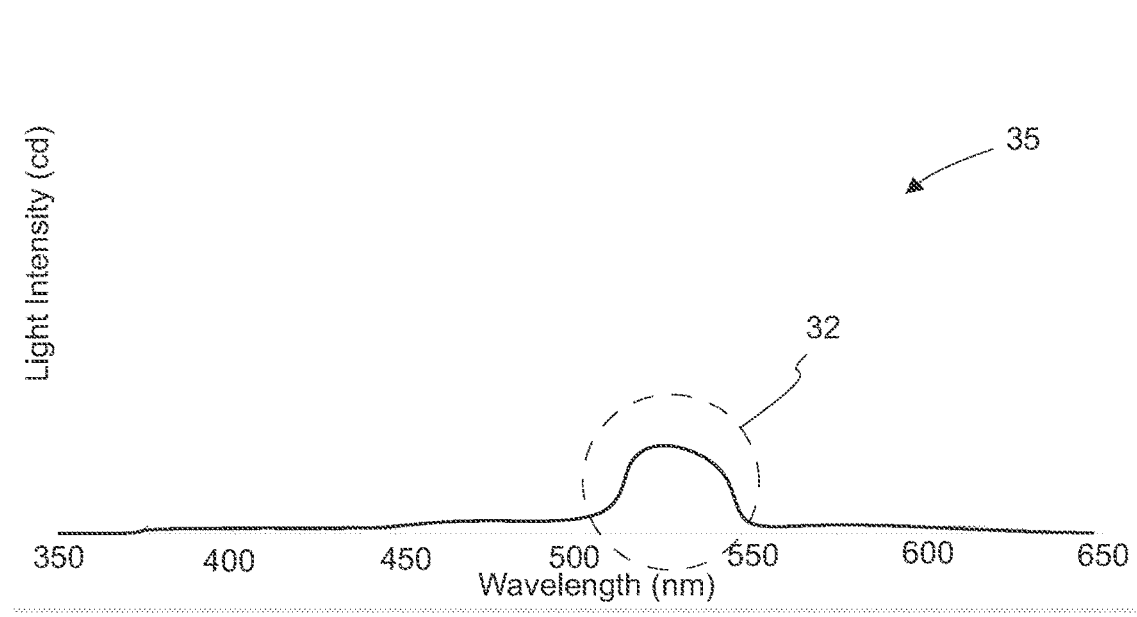
FIG. 3b shows a spectral response of an UV light reflected from the web containing a fluorescent liquid stain, detected by an imaging device comprising a green filter according to example embodiment of the device.

FIG. 3b shows a spectral response of an UV light 35 detected by an imaging device comprising a green filter according to example embodiment of the device. In this example also, fluorescent liquid is selected so that it emits fluorescent light between 520-550 nm. In this figure, the first intensity peak 31 is filtered and only the fluorescence peak 32 emitted by the fluorescent liquid around 520-550 nm is passed through.

Figure 4A:
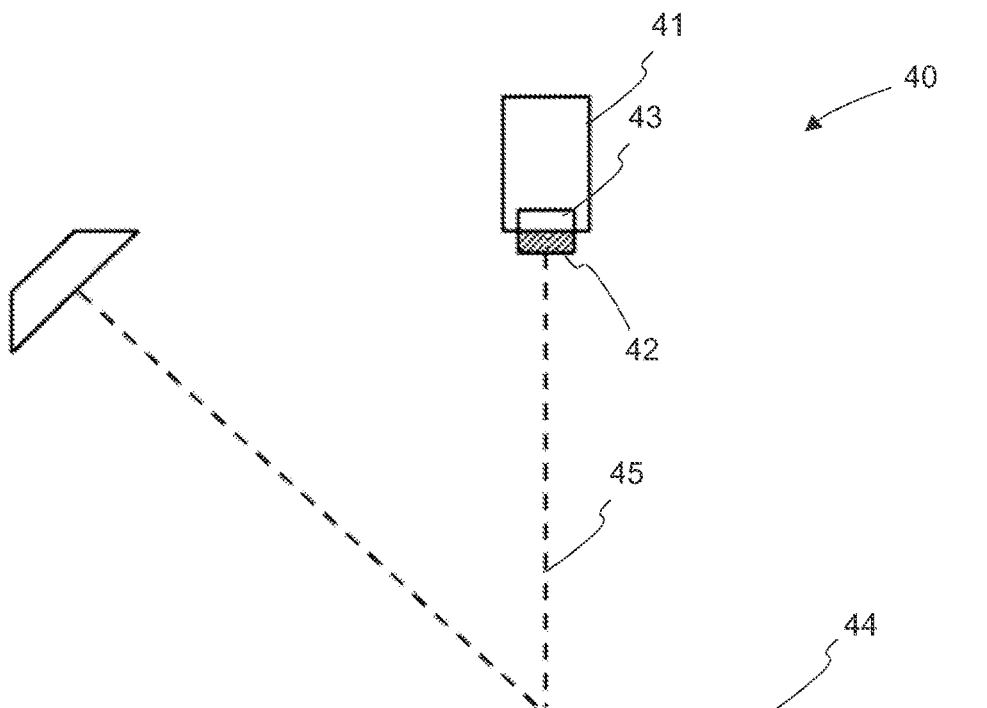
FIG. 4a, b show a machine vision system according to the example embodiment of the invention.

FIG. 4a shows a machine vision system 40 according to the example embodiment of the invention. The machine vision system 40 comprises an imaging device 41 with an additional colour filter 42 in front of an imaging sensor 43 of the imaging device 41 i.e. the additional filter 42 is arranged between the imaging sensor 43 and an imaging target 44 for filtering reflected UV light 45 from the imaging target 44.

Figure 4B:
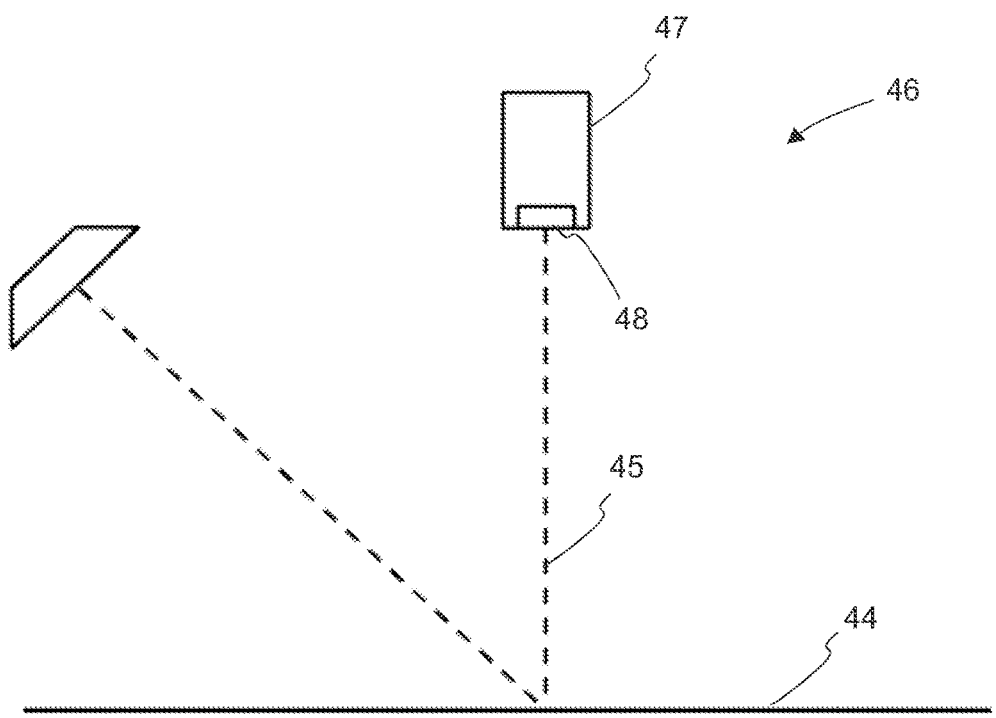

FIG. 4b shows a machine vision system 46 according to the example embodiment of the invention. The machine vision system 46 comprises an imaging device 47 with an imaging sensor 48. The imaging sensor 48 comprises a colour sensor as a filter and the colour sensor is arranged to filter non-green colours of reflected UV light 45 from the imaging target 44.

Figure 5:
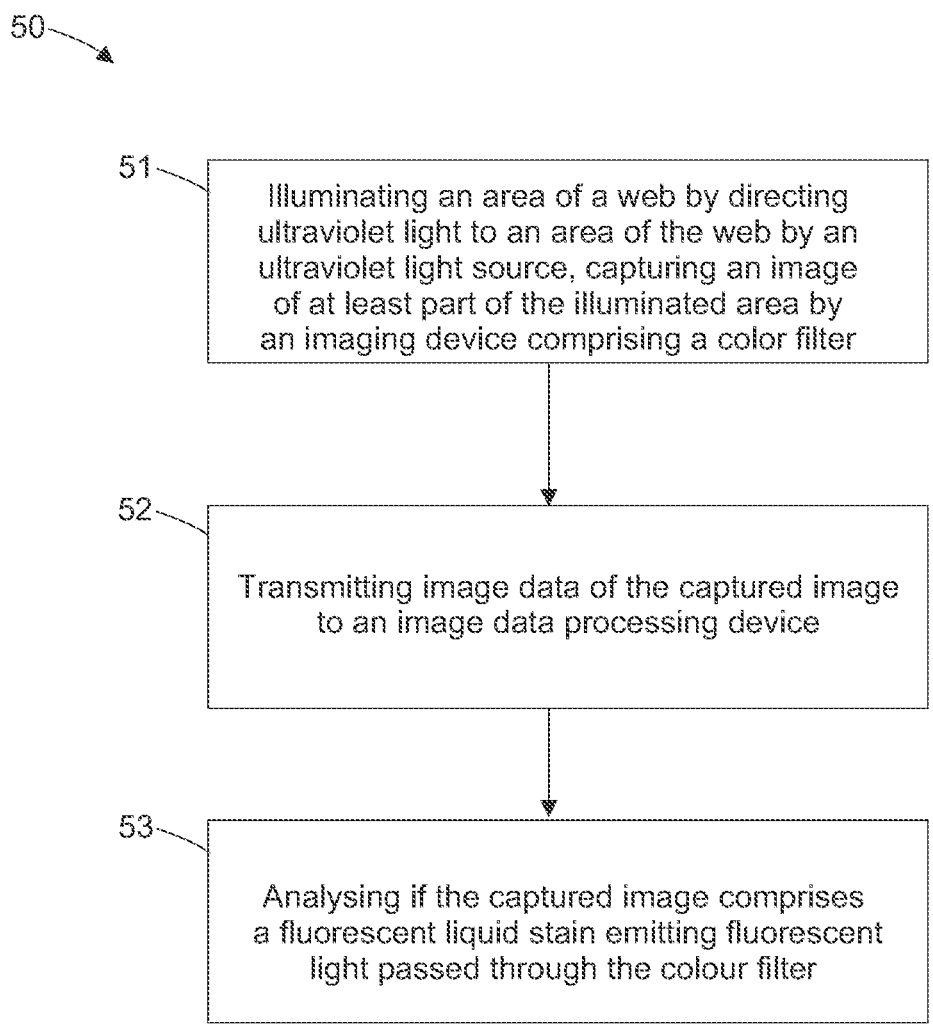
FIG. 5 shows a flow chart of a method for detecting fluorescent liquid from a wood fibre web by a machine vision system according to an embodiment of the invention.

FIG. 5 shows a flow chart of a method 50 for detecting fluorescent liquid from a wood fibre web by a machine vision system according to an embodiment of the invention. In step 51 an area of a wood fibre web is illuminated by directing ultraviolet light to an area of the web by an ultraviolet light source. In step 52 an image of at least part of the illuminated area is captured by an imaging device comprising a colour filter. In step 53 the captured image is analysed in order to detect if the captured image comprises a fluorescent liquid stain emitting fluorescent light passed through the colour filter.

Figure 6A:
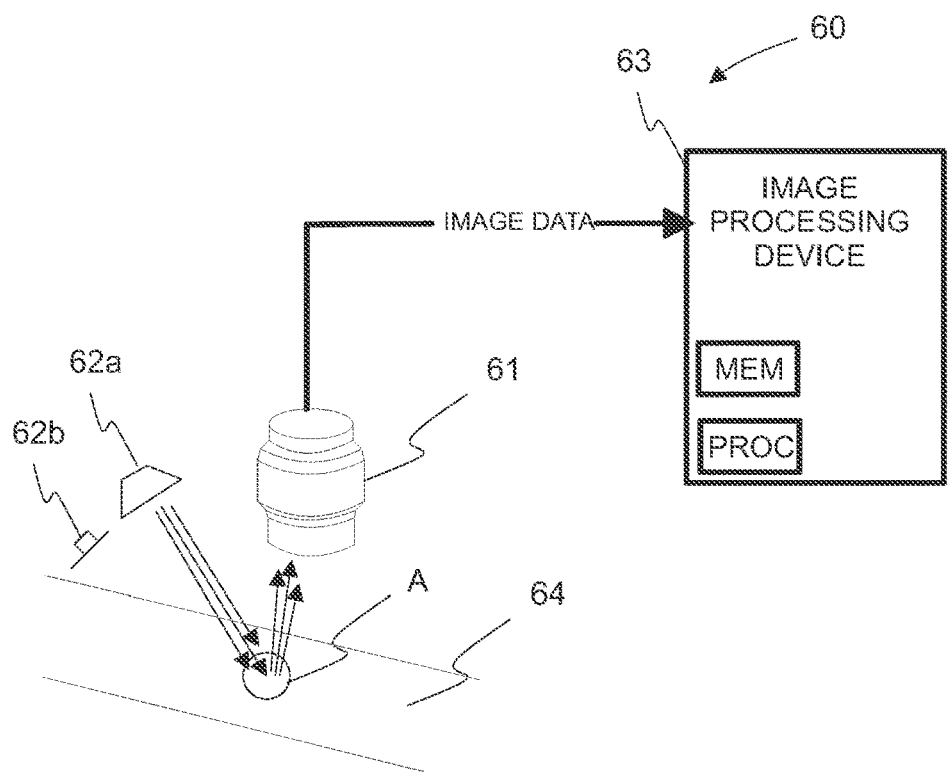
FIG. 6a, b show a machine vision system according to the example embodiment.
Figure 6B:
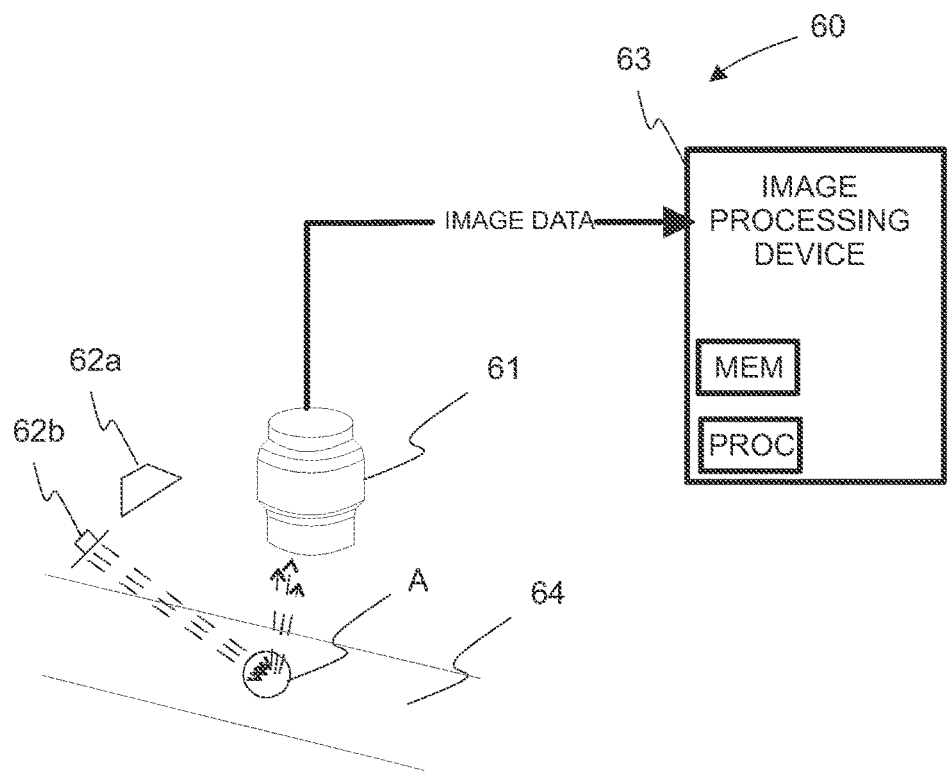

FIGS. 6a and 6b show a machine vision system according to the example embodiment of the invention. The machine vision system 60 of FIG. 6a comprises an imaging device 61 comprising a filter (not shown), an UV light source 62a, a non-UV light source 62b and an external image data processing device 63. The light sources 62a, 62b are arranged to illuminate an area of a web 64. The light sources 62a, 62b alternate so that every other captured image is illuminated with UV light and every other with regular non-UV light. The imaging device 61 may take two images of the same area with different illumination i.e. the first image of an area is captured with UV light and the second image of the same area is captured with non-UV light, or vice versa.

In FIG. 6a, the web is illuminated by the UV light source 62a and in FIG. 6b, the web is illuminated by the non-UV light source 62b. FIG. 6a shows also the UV light that is emitted by the UV light source 62a and FIG. 6b shows also the non-UV light that is emitted by the non-UV light source 62b. It is also shown, how the emitted UV light and non-UV light reflect to the imaging devices 61.

In these example embodiments, there is only one imaging device 61, one UV light source 62 and one non-UV light source 62b, however it is also possible for there to be two or more imaging devices 61 and/or UV light sources 62a and/or non-UV light sources 62b. In this example embodiment, the area comprises a non-fluorescent liquid stain A. After the imaging device 60 has captured an image, it transmits the image data to the external image data processing device 63. The image data processing device 63 is configured to analyse the image data that it receives in order to find fluorescent liquid stains of those images that are illuminated by the UV light source 62a and in order to find non-fluorescent deviations of those images that are illuminated by the non-UV light source 62b. If the external image data processing device 63 detects a fluorescent liquid stain(s) or some other deviation, it may trigger an alarm. The external image data processing device 63 may also be configured to detect other faults than fluorescent liquid stains of those images that are illuminated by the UV light source 62a and to detect fluorescent liquid stains of those images that are illuminated by the non-UV light source 62b and alarm about them.

Instead of the external image data processing device 63 the machine vision system 60 may comprise an integrated image data processing device that is configured to analyse the image data in order to find fluorescent liquid stains and non-fluorescent defects.

The various embodiments of the invention can be implemented with the help of computer program code that resides in a memory and causes an apparatus to carry out the invention. For example, the apparatus that is a computing device, for example, an image data processing device may comprise circuitry and electronics for analysing, receiving and transmitting data, a computer program code in a memory, and a processor which, when running the computer program code, causes the apparatus to carry out the features of an example embodiment. The processor, when running the computer program code may carry out all the steps of the following method: illuminating an area of a web by directing ultraviolet light to an area of the web by an ultraviolet light source, capturing an image of at least part of the illuminated area by an imaging device comprising a colour filter, for example green or red filter, transmitting image data of the captured image to an image data processing device, and analysing if the captured image comprises a fluorescent liquid stain emitting fluorescent light passed through the colour filter.

Considerable advantages are achieved by the present invention when compared to methods and systems of existing machine vision systems when detecting liquid stains. By means of the arrangement according to example embodiments of the invention it is possible to use one or more imaging device(s) and one or more UV light sources for reliably detecting liquid stains comprising fluorescent marker. It is important that liquid contaminated product is removed from the process in order to ensure the high quality of end product. In addition, when fluorescent marker is used in liquids, liquid stains can be more clearly differentiated from other faults in a web and the leaking machine is known to be looked for. As above explained, an effective way to detect liquid stains is to add a fluorescent marker to liquid of a machine(s) or use inherently fluorescent liquid, and monitor the wood fibre web passing through or in the vicinity of these machine(s) by one or more imaging devices equipped with an integral or additional colour filter for filtering the wavelength of UV light when one or more UV light source(s) illuminates the web. The filter is selected on the basis of the wavelength spectrum emitted by the used fluorescent liquid. The intensity level of the captured images may be increased before detecting fluorescent liquid stains.

It is obvious that the present invention is not limited solely to the above-presented embodiments, but it can be modified within the scope of the appended claims.

The invention claimed is:

1. A camera detection method for detecting a wood fibre web, the method comprising:
illuminating an area of the wood fibre web by directing ultraviolet light to an area of the web by an ultraviolet light source; capturing a first image of at least part of the ultraviolet illuminated area by an imaging device comprising a colour sensor, which is configured to filter reflected UV light from images illuminated by the ultraviolet light source; transmitting image data of the first image to an image data processing device; analysing if the first image comprises a fluorescent defect emitting fluorescent light passed through the colour sensor; wherein the method further comprises: illuminating the same area of the wood fibre web by directing non-ultraviolet light to the area of the web by a non-ultraviolet light source after capturing the first image; capturing a second image of at least part of the area illuminated with the non-ultraviolet illumination by the same imaging device; transmitting image data of the second image to the image data processing device; and analysing if the second image comprises a non-fluorescent defect, wherein the image data processing device is configured to find fluorescent defects from images illuminated by an ultraviolet light source and to find non-fluorescent defects from images illuminated by a nonultraviolet light source.

2. The method according to claim 1, wherein every other captured image is illuminated with the ultraviolet light and every other with the non-ultraviolet light.

3. The method according to claim 1, wherein a part of the captured images is illuminated with the ultraviolet light and the other part with the non-ultraviolet light.

4. The method according to claim 1, wherein the wood fibre web is a paper or cardboard web.

5. The method according to claim 1, wherein the colour sensor is a part of the imaging device or an imaging sensor of the imaging device.

6. The method according to claim 1, wherein the colour sensor is a green filter passing through wavelengths approximately 520-550 nm or a red filter passing through wavelengths approximately 640-730 nm, and wherein the fluorescent light emitted by the fluorescent liquid corresponds to wavelengths passed through the colour sensor.

7. The method according to claim 1, wherein the fluorescent liquid is produced by adding a fluorescent marker into liquid, or wherein the fluorescent liquid is inherently fluorescent.

8. The method according to claim 1, wherein the method further comprises increasing the intensity level of the captured image.

9. The method according to claim 1, wherein the non-fluorescent defects are holes, spots, streaks or wrinkles.

10. The method according to claim 1, wherein the method further comprises simultaneous detecting an edge of the web.

11. A camera detection machine vision system for detecting a wood fibre web wherein, the machine vision system comprises
an image data processing device, which is configured to find fluorescent defects from images illuminated by an ultraviolet light source and to find non-fluorescent defects from images illuminated by a non-ultraviolet light source, an imaging device comprising a colour sensor, which is configured to filter reflected UV light from images illuminated by the ultraviolet light source, and an ultraviolet light source, which is configured to direct ultraviolet light to an area of the web, wherein the imaging device is configured to capture a first image of the ultraviolet illuminated area with the colour sensor and to transmit image data of the first image to the image data processing device for analysing if the first image comprises a fluorescent liquid defect emitting fluorescent light at wavelength spectrum passing through the colour sensor, wherein the machine vision system further comprises a non-ultraviolet light source that is after capturing the first image configured to direct non-ultraviolet light to the same area of the wood fibre web than the ultraviolet light source, and that the imaging device is further configured to capture a second image of at least part of the area illuminated with the non-ultraviolet illumination by the same imaging device, and to transmit the image data of the second image to the image data processing device for analysing if the second image comprises a non-fluorescent defect.

12. The machine vision system according to claim 11, wherein every other captured image is illuminated with ultraviolet light and every other with non-ultraviolet light.

13. The machine vision system according to claim 11, wherein a part of the captured images is illuminated with ultraviolet light and the other part with nonultraviolet light.

14. The machine vision system according to claim 11, or wherein the colour sensor is a part of the imaging device or an imaging sensor of the imaging device.

15. The machine vision system according to claim 11, wherein the colour sensor acts as a green filter passing through wavelengths approximately 520-550 nm or a red filter passing through wavelengths approximately 640-730 nm, and wherein the fluorescent light emitted by the fluorescent liquid corresponds to wavelengths passed through the colour sensor, and wherein the fluorescent light emitted by the fluorescent liquid corresponds to wavelengths.

16. The machine vision system according to claim 11, wherein the fluorescent liquid is produced by adding a fluorescent marker into liquid or wherein the fluorescent liquid is inherently fluorescent.

17. The machine vision system according to claim 11, wherein the non-fluorescent defects are holes, spots, streaks or wrinkles.

18. The machine vision system according to claim 11, wherein the non-ultraviolet light source is a LED.

19. At least one memory storing instructions to execute the method of claim 1.

20. The method according to claim 1, wherein the configuration of the image data processing device to find fluorescent or non-fluorescent defects comprises adjusting of intensity level of captured images.

21. The machine vision system according to claim 11, wherein the configuration of the image data processing device to find fluorescent or non-fluorescent defects comprises adjusting of intensity level of captured images.

* * * * *